United States Patent

Schneider et al.

[11] 4,153,446
[45] May 8, 1979

[54] HERBICIDAL N-(HALOACETYL)-N'-METHYLENEPYR- ROLIDONYL)-2-CYCLOALKOXYANILINES

[75] Inventors: Louis Schneider, Elizabeth; David E. Graham, Westfield, both of N.J.

[73] Assignee: GAF Corporation, New York, N.Y.

[21] Appl. No.: 942,644

[22] Filed: Sep. 15, 1978

[51] Int. Cl.² .................... C07D 207/26; A01N 9/22
[52] U.S. Cl. .................. 71/95; 260/326.43; 260/326.5 C; 260/568; 260/645
[58] Field of Search .................. 260/326.43; 71/95

[56] References Cited

U.S. PATENT DOCUMENTS 3,769,301  10/1973  Olin .................. 260/326.45

Primary Examiner—Donald G. Daus
Assistant Examiner—Lisa Jones
Attorney, Agent, or Firm—Walter C. Kehm; Walter Katz

[57] ABSTRACT

Herbicidal compounds having the formula:

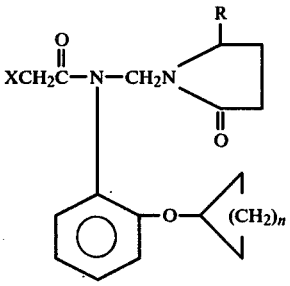

where
n=0-3,
R is hydrogen or alkyl of 1-3 carbon atoms, and
X is chloro or bromo,
are provided herein.

The compounds of the invention are effective herbicides, particularly against wild grasses.

9 Claims, No Drawings

HERBICIDAL N-(HALOACETYL)-N'-METHYLENEPYRROLIDONYL)-2-CYCLOALKOXYANILINES

BACKGROUND OF THE INVENTION

1. Field of the Invention

This invention relates to novel N-(haloacetyl)-N-(N'-methylenepyrrolidonyl)-2-cycloalkoxyanilines which are useful herbicides.

2. Description of the Prior Art

U.S. Pat. Nos. 3,769,301 and 3,907,544 disclose related N-(acyl-tert-amidoalkyl)acetanilides, including N-methylenepyrrolidonyl derivatives; however, these compounds are substituted with 2,6-dialkyl groups only.

SUMMARY OF THE INVENTION

This invention describes herbicidal N-(haloacetyl)-N-(N'-methylenepyrrolidonyl)-2-cycloalkoxyanilines having the formula:

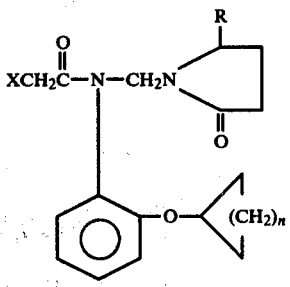

where
n=0–3,
R is hydrogen or alkyl of 1–3 carbon atoms, and,
X is chloro or bromo.

DETAILED DESCRIPTION OF THE PREFERRED EMBODIMENTS

The herbicidally active compounds of the present invention may be obtained by a four-step process. In the first step, 2-nitrophenol is reacted with a cycloalkyl halide in the presence of an acid acceptor to yield a 2-cycloalkoxy-nitrobenzene. In the second step, the nitro group is reduced to the corresponding aniline. The third step of the process comprises reacting the aniline with an N-methylolpyrrolidone to form the corresponding N-(N'-methylenepyrrolidonyl) intermediate. Finally, in step four, the intermediate is suitably acylated with a haloacetyl halide to form the desired compounds.

As used herein, the term "alkyl" includes both straight and branched chained hydrocarbons.

The compounds of this invention are especially useful as agricultural herbicides. They show particularly effective herbicidal activity against wild grasses, such as Japanese millet, foxtail millet and crabgrass.

Usually they are applied to the soil at the rate of about 1 to 25 lbs. per acre, or as a foliar spray on the weeds at concentrations of about 30 to 260 ppm., depending on various circumstances of the susceptibility of the weed to the herbicide, the weather, the stage of growth and various other factors. The material also may be applied as a dust. As a dust, it is practical to extend it with diluents, such as bentonite, chalk, clay, diatomaceous earth, fullers earth, mica, ground slate or any of the other usual carriers for agricultural chemicals.

As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

Following are examples of preparation of the compounds of the invention and are present by way of illustration and are not intended to be limiting unless otherwise specified.

EXAMPLE 1

N-Chloroacetyl-N-(N'-Methylenepyrrolidonyl)-2-Cyclopentoxyaniline

A. 2-Cyclopentoxynitrobenzene

2-Nitrophenol (83.5 g, 0.60 mole), cyclopentyl bromide (98.0 g, 0.66 mole), anhydrous potassium carbonate (82.9 g, 0.60 mole) and dry acetone (600 cc) were refluxed for 72 hrs., and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 144°–146° C. at 1.0 mm. Hg to yield 58.2 g of product (46.8%).

B. 2-Cyclopentoxyaniline

Iron 60 mesh (51.9 g, 0.93 mole), water (220 cc), ethanol (244 cc) and concentrated hydrochloric acid (14.2 cc) were heated to reflux under a nitrogen blanket. Then 2-cyclopentoxynitrobenzene (55.2 g, 0.27 mole) was added at reflux over a period of 2 hrs. The reaction was maintained at reflux for an additional 3 hrs. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 126°–130° C. at 2.0–2.5 mm. Hg to yield 30.3 g (64.3%) of product.

C. N-Methylenepyrrolidonyl-2-Cyclopentoxyaniline

2-Cyclopentoxyaniline (10.0 g, 0.057 mole), N-methylolpyrrolidone (9.75 g, 0.85 mole) and xylene (25 cc) were refluxed under azeotropic conditions with the removal of 1.5 cc of water. The xylene was removed by rotary evaporation and the product was crystallized from 100 cc of hexane to yield 8.0 g (51.6%) of product, m.p. 87°–87.5° C.

D. N-Methylenepyrrolidonyl-2-cyclopentoxyaniline (7.0 g, 0.026 mole), toluene (70 cc) and sodium carbonate (3.0 g, 0.028 mole) were cooled to 5° C. and chloroacetyl chloride (3.0 g, 0.027 mole) in toluene (20 cc) was added at 5° C. in 1 hr. The temperature was allowed to rise to 25° C. and the mixture was stirred at 25° C. for 20 hrs. The reaction mixture then was washed with 100 cc of water. The toluene was removed by rotary evaporation, and the crude product was crystallized from ether to yield 6.0 g (67.0%) of product, m.p. 84°–85° C.

EXAMPLE 3

N-Chloroacetyl-N-(N'-Methylenepyrrolidonyl)-2-Cyclopropoxyaniline

In a similar manner as in Example 1, bromocyclopropane was reacted with o-nitrophenol to yield 2-cyclopropoxynitrobenzene; which was reduced to the corresponding aniline; reacted with N-methylolpyrrolidone to form the corresponding N-methylenepyrrolidonyl derivative; and acetylated with chloroacetyl chloride to form the desired product.

EXAMPLE 4

N-Chloroacetyl-N-(N'-Methylenepyrrolidonyl)-2-Cyclohexoxyaniline

In a similar manner as in Example 1, bromocyclohexane was reacted with o-nitrophenol to yield 2-cyclohexoxynitrobenzene; which was reduced to the corresponding aniline; then reacted with N-methylolpyrrolidone to form the corresponding N-methylenepyrrolidonyl derivative; which was acylated with chloroacetyl chloride to form the desired product.

EXAMPLE 5

N-Chloroacetyl-N-(5-Methyl-N'-Methylenepyrrolidonyl)-2-Cyclopentoxyaniline

In a similar manner as in Example 1, bromocyclopentane was reacted with o-nitrophenol to yield 2-cyclopentoxynitrobenzene; which was reduced to the corresponding aniline; then reacted with N-methylol-5-methylpyrrolidone to form the corresponding N-5-methyl-N-methylenepyrrolidonyl derivative; which was acylated with chloroacetyl chloride to form the desired product.

TABLE 1

| Test Plant | Pre-Emergence Herbicidal Rating Primary (10 lbs/acre) | |
| --- | --- | --- |
|  | Example 1 | Standard (Diuron) |
| Foxtail Millet | 7 | 10 |
| Japanese Millet | 10 | 10 |
| Crabgrass | 10 | 10 |

The tests demonstrate the effectiveness of the compounds of the invention against representative wild grasses.

While the invention has been described with particular reference to certain embodiments thereof, it will be understood that certain modifications and changes may be made which are within the skill of the art. Therefore it is intended to be bound only by the appended claims.

What we claim is:

1. Herbicidal compounds having the formula:

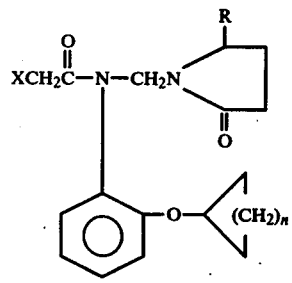

where
n=0-3,
R is hydrogen or alkyl of 1-3 carbon atoms, and,
X is chloro or bromo.

2. Compounds according to claim 1 wherein n is 2.

3. Compounds according to claim 1 wherein R is hydrogen.

4. A compound according to claim 1 which is N-chloroacetyl-N-(N'-methylenepyrrolidonyl)-2-cyclopentoxyaniline.

5. A compound according to claim 1 which is N-chloroacetyl-N-(N'-methylenepyrrolidonyl)-2-cyclobutoxyaniline.

6. A compound according to claim 1 which is N-chloroacetyl-N-(N'-methylenepyrrolidonyl)-2-cyclohexoxyaniline.

7. A compound according to claim 1 which is N-chloroacetyl-N-(5-methyl-N'-methylenepyrrolidonyl)-2-cyclopentoxyaniline.

8. A compound according to claim 1 which is N-chloroacetyl-N-(N'-methylenepyrrolidonyl)-2-cyclopropoxyaniline.

9. A herbicidal composition consisting essentially of a compound of the formula according to claim 1, and an inert carrier therefor.

* * * * *